United States Patent [19]

Poss et al.

[11] Patent Number: 5,552,533
[45] Date of Patent: Sep. 3, 1996

[54] PREPARATION OF (8S)-8-FLUOROERYTHROMYCINS WITH N-F FLUORINATING AGENTS

[75] Inventors: Andrew J. Poss, Kenmore; George A. Shia, Amherst, both of N.Y.

[73] Assignee: AlliedSignal Inc., Morris County, N.J.

[21] Appl. No.: 305,626

[22] Filed: Sep. 14, 1994

[51] Int. Cl.$^6$ ............................ C07H 17/08; C07H 15/24
[52] U.S. Cl. ............................ 536/7.2; 536/7.5; 536/18.1
[58] Field of Search ........................... 536/7.2, 18.1, 536/7.5

[56] References Cited

U.S. PATENT DOCUMENTS

| | | | |
|---|---|---|---|
| 3,674,773 | 7/1972 | Kurath et al. | 260/210 E |
| 4,514,562 | 4/1985 | Toscano | 536/7.2 |
| 4,673,736 | 6/1987 | Toscano | 536/7.2 |
| 4,935,519 | 6/1990 | Van Der Puy et al. | 546/13 |
| 4,973,697 | 11/1990 | Umemoto et al. | 546/295 |
| 5,081,249 | 1/1992 | Umemoto | 546/294 |
| 5,086,178 | 2/1992 | Banks | 544/351 |
| 5,116,982 | 5/1992 | Fung et al. | 546/13 |
| 5,254,732 | 10/1993 | Differding | 564/82 |
| 5,288,930 | 2/1994 | Shields et al. | 570/179 |

FOREIGN PATENT DOCUMENTS 0177030  4/1986  European Pat. Off. ........ C07H 17/08

OTHER PUBLICATIONS

J. H. J. Peet et al. B. W. 2–Fluoro[(Dimethylamino)Methyl] Ferrocene. A Warning. *Journal of Organometallic Chemistry*, 82 (1974) C57–C58.

W. Adcock et al. Perchloryl Fluoride: A Further Warning. *Journal of Organometallic Chemistry*, 91 (1975) C20.

G. Sankar Lal. Site–Selective Fluorination of Organic Compounds Using 1–Alkyl–4–fluoro–1,4–diazabicyclo[2.2.2] octane Salts (Selectfluor Reagents). *J. Org. Chem.* 1993, 58, 2791–2796.

T. Umemoto et al. Power and Structure–Variable Fluorinating Agents. The N–Fluoropyridinium Salt System. *J. Am. Chem. Soc.* 1990, 112, 8563–8575.

V. Murtagh. Electrophilic Fluorination: An Introduction. *Performance Chemicals.* Aug./Sep. 1991,36.

V. Murtagh. Further Progress on Electro–fluorination. *Performance Chemicals.* Aug./Sep. 1992, 27.

G. G. Furin. Some "Electrophilic Fluorination Agents" in L. German and S. Zemskov (eds.) *New Fluorinating Agents in Organic Systhesis*. Springer Verlag, Berlin (1989) 35.

E. Differding et al. N–Fluoro–benzene–sulfonimide—A Practical Reagent for Electrophilic Fluorinations. *Synthetic Letters* 187 (1991).

F. Davis et al. N–Fluoro–O–Benzenedisulfonimide: A Useful New Fluorinating Reagent. *Tetrahedron Letters.* vol. 32, No. 13 (1991), pp. 1631–1634.

R. Eric Banks et al. 1–Alkyl–4–fluoro–1,4–diazoniabicyclo [2.2.2]octane Salts: a Novel Family of Electrophilic Fluorinating Agents. *J. Chem. Soc., Chem. Commun.*, 1992, pp. 595–596.

N. N. Aleinikov et al. Synthesis and characterization of N–fluoroalkylsulfonamides. *Journal of Fluorine Chemistry*, vol. 58 (1992), p. 141.

Selectfluor™ Reagents: N–Fluoro Triethylenediamine Derived Compounds of High Fluorinating Efficiency and Selectivity (Product Literature of Air Products and Chemicals, Inc.). No date.

*J. Org. Chem.*, vol. 56, 1991 pp. 5962–5964.

*Primary Examiner*—John W. Rollins
*Attorney, Agent, or Firm*—Jay P. Friedenson

[57] ABSTRACT

(8S)-8-fluoroerythromycins are prepared by reacting 8,9-anhydroerythromycin 6,9-hemiacetals or an N-oxide thereof with a carboxylic acid and an N-F fluorinating agent. The anhydro starting material may be prepared in situ from erythromycins or an N-oxide derivative thereof. The (8S)-8-fluoroerythromycin products are useful antibacterial agents.

22 Claims, No Drawings

PREPARATION OF (8S)-8-FLUOROERYTHROMYCINS WITH N-F FLUORINATING AGENTS

FIELD OF THE INVENTION

The present invention relates to a process for the synthesis of (8S)-8-fluoroerythromycins which are well known as useful antibacterial agents and are described in U.S. Pat. Nos. 4,673,736 and 4,514,562.

BACKGROUND OF THE INVENTION

The current methods for preparing (8S)-8-fluoroerythromycins involve either treatment of 8,9-anhydroerythromycin 6,9-hemiacetals or their N-oxides with fluorinating agents such as perchloryl fluoride, fluoroxyperfluoroalkanes, fluoroxysulfurpentafluoride, molecular fluorine, lead tetracetate/hydrogen fluoride or trifluoroacetylhypofluorite (U.S. Pat. No. 4,514,562). More recently, the preparation of (8S)-8-fluoroerythromycins has been improved by exposure of erythromycin to perchloryl fluoride in an acetic acid buffer and an inert co-solvent (U.S. Pat. No. 4,673,736). The aforementioned fluorinating agents have disadvantages; such as: hazards in handling, relatively high cost, the need for special reaction vessels, and chemical instability, which make them unsatisfactory for preparing commercial quantities of (8S)-8-fluoroerythromycins. Perchloryl fluoride, in particular, is known to form unstable and explosive organoperchlorates in reactions with organic molecules. See Peet, H. H. J. and Rocket, B. W. J. Organometal. Chem. 82, C57 (1974) and Adcock, W. and Khor, J. C. ibid. 91, C20 (1975).

N-F (electrophilic) fluorinating agents, characterized by a structure containing an N-F bond, are a well known class of reagents for introducing fluorine into organic molecules. As a class, they have been shown to be stable due to their ability to be stored for long periods of time and high melting points and are easily handled reagents.

The fluorination of double bonds in various organic compounds with N-F fluorinating agents is reported in J. Am. Chem. Soc. 112, 8563 (1990) and J. Org. Chem. 1993, 58, 2791–2796. The conditions reported for such N-F fluorinations include use of an organic solvent such as acetonitrile, dichloromethane and tetrahydrofuran and an oxygen containing nucleophilic reagent such as acetic acid. When these standard N-F fluorination conditions were used to attempt to fluorinate 8-fluoroerythromycin or 8,9-anhydroerythromycin, poor yields of 8S-8-fluoroerythromycins were obtained.

SUMMARY OF THE INVENTION

This invention relates to a process for preparing (8S)-8-fluoroerythromycins comprising reacting 8,9-anhydroerythromycin 6,9-hemiacetals or an N-oxide thereof with a carboxylic acid and an N-F fluorinating agent for a sufficient time and temperature to obtain an (8S)-8-fluoroerythromycin. An additional embodiment of the invention comprises preparing the 8,9-anhydroerythromycin 6,9-hemiacetal starting material from erythromycin or an N-oxide derivative thereof and using same in situ for the reaction to form the (8S)-8-fluoroerythromycin. The reaction avoids the use of materials which are characteristically hazardous and/or expensive, while removing the need for a co-solvent.

DETAILED DESCRIPTION OF THE INVENTION

According to the invention, erythromycin, or an N-oxide thereof is reacted with an N-F fluorinating agent in the presence of a carboxylic acid.

N-F fluorinating agents are a well known class of organic compounds which are characterized by an N-F bond. These compounds can also be substituted with a variety of substituents which do not interefere with the fluorination reaction. Examples of substituents which may be present on the N-F fluorinating agents which do not interfere with the fluorination reactions include, for example, alkyl, alkoxy, Cl, Br, F, haloalkyl, phenyl, cycloalkyl and cyano. The N-F fluorinating agent can contain radioactive $^{18}F$ in lieu of $^{19}F$ to give radiolabelled products.

Illustrative of the compounds included within this well known class of N-F is fluorinating agents are N-fluorobenzenesulfonimide (NFSi) and derivatives (U.S. Pat. No. 5,116,982), N-fluoromethanesulfonimide and derivatives, N-fluoropyridinium pyridine heptafluorodiborate (NFPy), 1-chloromethyl-4-fluoro-1,4-diazoniabicyclo[2.2.2]octane bis(tetrafluoroborate) [F-TEDA] and other 1-alkyl-4-fluoro-1,4-diazoniabicyclo[2.2.2]octane salts and fluorinated diazabicycloalkane derivatives thereof (U.S. Pat. No. 5,086,178), 1-hydroxyl-4-fluoro-1,4-diazoniabicyclo[2.2.2]octane bis(tetrafluoroborate) [NFTh], and other fluorinated derivatives thereof (U.S. Pat. No. 5,459,267), N-alkyl-N-fluoro-p-toluenesulphonamides, N-fluoro-o-benzene-disulfonimide, N-fluoro-N-alkylsulfonamides, N-fluoropyridinium sulfonates (U.S. Pat. No. 5,081,249), perfluoro-N-fluoro-N-(4-pyridyl)methanesulphonamide and various substituted N-fluoropyridinium salts. Properties of these various species of N-F fluorinating agents have been reviewed by V. Murtagh [in "Further Progress on Electro-fluorination," Performance Chemicals, p 27, August/September 1992.]; G. G. Furin, [in L. German and S. Zemskov (eds.) New Fluorinating Agents in Organic Synthesis, Springer Verlag, Berlin (1989)35] and by T. Umemoto, et. al. [in "Power and Structure-Variable Fluorinating Agents. The N-Fluoropyridinium Salt System", J. Am. Chem. Soc. 112, 8563 (1990)]; "N-Fluorobenzenesulfonimide: A Practical Reagent for Electrophilic Fluorinations" by Differding, E.; Ofner, H. Synthetic Letters 187 (1991); N-Fluoro-o-benzenedisulfonimide by Davis, F. A.; Han W. in "N-Fluoro-o-Benzenedisulfonimide: A Useful New Fluorinating Reagent" Tetrahedron Letters 32, 1631 (1991); "N-Fluoropyridinium Salts Having Trichloromethyl Substituents" by Fung, A. P. et. al. U.S. Pat. No. 5,116,982 and 1-alkyl-4-fluoro-1,4-diazoniabicyclo[2.2.2]octane salts by Banks, R. E.; et.al. J. Chem. Soc., Chem. Commun. 595 (1992). A preferred class of N-F fluorinating agent is represented by the broad-class of N-F fluorinating agents defined which do not contain a pyridine nucleus. The preferred N-F fluorinating agents are the fluorinated diazabicycloalkane compounds described in U.S. Pat. No. 5,086,178, the N-fluorobenzenesulfonimides described in U.S. Pat. No. 5,254,732, the 1-substituted-4-fluoro-1,4-diazoniabicyclo[2.2.2]octane salts described in co-pending, commonly assigned application Ser. No. 173, 297, filed Dec. 23, 1993, now U.S. Pat. No. 5,459,267 which is incorporated by reference herein, and N-fluorodimethylsulfonimide and derivatives as referred to in Journal of Fluorine Chemistry, 58, page 141, 1992.

The carboxylic acid may be any compound having a —COOH functionality, but is preferably a branched or straight chain carboxylic acid, which may be substituted with a variety of substituents such as halogens, electron donating or electron withdrawing groups, having a pKa which is less than or equal to that of acetic acid. Still preferably, the carboxylic acid has from 2–8 carbon atoms and, most preferably, is acetic acid. The concentration of the carboxylic acid in the reaction mixture is preferably about 0.05M to 1.5M and about 0.25M, to 0.5M. Preferably, the process is conducted in the absence of an inert co-solvent, such as used in the prior art N-F fluorinating reactions, e.g. tetrahydrofuran, acetonitrile or methylene chloride. The carboxylic acid is preferably buffered to a pH of about 4–7 and, more preferably, about 4–4.5 with any suitable buffering agent such as an alkali metal hydroxide, e.g. NaOH, KOH or LiOH.

Good yields of the fluoroerythromycin products are obtained when 8,9-anhydroerythromycin 6,9-hemiacetals or the corresponding N-oxides are reacted with N-F fluorinating agents in accordance with the invention. The anhydro reactant is reacted with at least about one molar equivalent of an N-F fluorinating agent for about 1 to about 30 hours, preferably, about 10 to about 24 hours. The reaction is preferably conducted at a temperature ranging from about −5° to about 50° C. at atmospheric pressure, still preferably, at about 10° to about 35° C., with about 23° C. or room temperature being the temperature most preferred. Preferably, the fluorination step is conducted at a pH of about 4 to about 7 and, more preferably, at a pH of about 4 to about 4.5.

In another embodiment of the invention, the 8,9-anhydroerythromycin 6,9-hemiacetals or the corresponding N-oxides are prepared as unisolated reaction intermediates by the action of a carboxylic acid on erythromycin or the corresponding N-oxides. A solution of erythromycin or the corresponding N-oxides dissolved in the carboxylic acid is allowed to mix as needed to form the anhydro derivative. Preferably, the reaction time is from about 1 minute to about 24 hours and, still preferably, from about 2 hours to about 4 hours. The anhydro formation takes place at a reaction temperature of about −5° to about 50° C. Preferably, the reaction temperature is about 20° to about 30° C. The anhydro unisolated intermediate may then be used in situ to prepare the fluoroerythromycin with an N-F fluorinating agent as described above.

Once the fluoroerythromycin is formed, conventional separation techniques can be employed to isolate the desired product. These methods include phase separation, vacuum filtration and solvent washing.

EXAMPLE 1

Preparation of (8S)-8-fluoroerythromycin A from erythromycin A with N-fluorobenzenesulfonimide in buffered acetic acid (sodium salt)

Erythromycin A (5 g, 6.813 mmole) was dissolved in glacial acetic acid (20 mL) at room temperature and stirred for 2 hours. The pH of the mixture was adjusted to 4.3 with 6N sodium hydroxide (approx. 12.5 mL) while the temperature was maintained below 20° C. N-fluorobenzenesulfonimide (2.2 g, 6.813 mmole) was added and stirring continued for an additional 18 hours at 22° C. Methylene chloride (100 mL) was added, the solution was placed in an ice bath while the pH of the mixture was adjusted to 9 with 6N sodium hydroxide (approx. 85 mL) and the temperature was maintained below 20° C. Next, water (100 mL) was added, the layers separated and the aqueous layer washed an additional two times with methylene chloride (100 mL each). The methylene chloride serves as an extractant for the flurithromycin product. The combined organic phases were washed 2 to 4 times with 5 percent sodium hydroxide (100 mL each) and dried over magnesium sulfate. After filtration, the organic phase was concentrated under vacuum at room temperature to afford 4.91 g of crude flurithromycin. The crude material was dissolved in ethanol concentrated to 20 mL. This process was repeated two more times. After standing at 0° C. for one night, the product was filtered under vacuum, washed with 5 mL cold ethanol and dried under vacuum at 40° C. to afford 3.48 g (68% yield) of flurithromycin ((8S)-8-fluoroerythromycin).

EXAMPLE 2

Preparation of (8S)-8-fluoroerythromycin A from erythromycin A with N-fluorobenzenesulfonimide in glacial acetic acid Erythromycin A (5 g, 6.813 mmole) and N-fluorobenzenesulfonimide (2.2 g 6,813 mmole) were dissolved in glacial acetic acid (20 mL) at room temperature and stirred for 18 hours. The reaction was worked-up in the same manner as Example 1 to afford 4.96 g of crude flurithromycin. This material was recrystallized as described in Example 1 to yield 2.25 g (44% yield) of flurithromycin. This example shows that reasonably good yields of flurithromycin may be obtained in the process of the invention without buffering.

EXAMPLE 3

Preparation of (8S)-8-fluoroerythromycin A from erythromycin A with N-fluorobenzenesulfonimide in acetic acid Erythromycin A (3 g, 4.1 mmole) was dissolved in glacial acetic acid (12 mL) at room temperature and stirred for 2 hours. N-fluorobenzenesulfonimide (1.6 g, 4.1 mmole) was added and stirring continued for an additional 4 hours at 22° C. The reaction was worked-up in the same manner as Example 1 to afford 2.533 g of crude flurithromycin. This material was recrystallized as described in Example 1 to yield 0.8 g (26% yield) of flurithromycin. This example shows the embodiment of the invention where the anydro derivative of erythromycin is prepared as an unisolated reaction intermediate and the N-F fluorination reaction is carried out without a buffer.

EXAMPLE 4

Preparation of (8S)-8-fluoroerythromycin A from erythromycin A with N-fluoro, N-chloromethyl triethylenediamine bis(tetrafluoroborate) in (unbuffered) glacial acetic acid Erythromycin A (1 g, 1.363 mmole) and N-fluoro, N-chloromethyl triethylenediamine bis(tetrafluoroborate) (0.46 g, 1.3 mmole) were dissolved in glacial acetic acid (4 mL) at room temperature and stirred for 5 hours. The reaction was worked up in the same manner as Example 1 to afford 1.16 g (74% yield) of crude flurithromycin.

EXAMPLE 5

Preparation of (8S)-8-fluoroerythromycin A from erythromycin A with 1-chlorormethyl-4-fluoro-1,4-diazoniabicyclo[2.2.2]bis(tetrafluoroborate) in buffered acetic acid Erythromycin A (5 g, 6.813 mmole) was dissolved in glacial acetic acid (20 mL) at room temperature and stirred for 2 hours. The pH of the mixture was adjusted to 4.3 with 6N sodium hydroxide (approx. 12.5 mL) while the temperature was maintained below 20° C. 1-Chloromethyl-4-fluoro-1,4-diazoniabicyclo[2.2.2]octane bis(tetrafluoroborate) (2.4 g, 6.813 mmole) was added and stirring continued for an additional 3 hours at 22° C. The reaction was worked up in the same manner as Example 1 to afford 4.5 g of crude flurithromycin. This material was recrystallized as described in Example 1 to yield 2.6 g (51% yield) of flurithromycin.

EXAMPLE 6

Preparation of (8S)-8-fluoroerythromycin A from erythromycin A with N-fluoropyridinium pyridine heptafluorodiborate Erythromycin A (0.5 g, 0.681 mmole) was dissolved in glacial acetic acid (4 mL) at room temperature and stirred for 2 hours. The pH of the mixture was adjusted to 4.3 with 6N sodium hydroxide (approx. 1.2 mL) while the temperature was maintained below 20° C. N-fluoropyridinium pyridine heptafluorodiborate (0.25 g, 0.75 mmole) was added and stirring continued for an additional 2 hours at 22° C. The reaction was worked up in the same manner as Example 1 to afford an 11% yield of crude flurithromycin. Although the yield was only 11%, this example demonstrates operation of the invention with N-F fluorinating agents derived from pyridine since with a co-solvent no flurithromycin is formed. (See Comparative Example 4).

EXAMPLE 7

Preparation of (8S)-8-fluoroerythromycin A from erythromycin A with 1-hydroxyl-4-fluoro-1,4-diazoniabicyclo[2.2.2]octane bis(tetrafluoroborate), NFTh, in buffered acetic acid (sodium salt)

Erythromycin A (5 g, 6.813 mmole) was dissolved in glacial acetic acid (20 mL) at room temperature and stirred for 2 hours. The pH of the mixture was adjusted to 4.3 with 6N sodium hydroxide (approx. 12.5 mL) while the temperature was maintained below 20° C. 1-Hydroxyl-4-fluoro-1,4-diazoniabicyclo[2.2.2]octane bis(tetrafluoroborate) (2.2 g, 6.813 mmole) was added and stirring continued for an additional 18 hours at 22° C. Methylene chloride (100 mL) was added, the solution placed in an ice bath while the pH of the mixture was adjusted to 9 with 6N sodium hydroxide (approx. 85 mL) and the temperature maintained below 20° C. Next, water (100 mL) was added, the layers separated and the aqueous layer washed an additional two times with methylene chloride (100 mL each). The methylene chloride serves as an extractant for the flurithromycin product. The combined organic phases were washed 2 to 4 times with 5% sodium hydroxide (100 mL each) and dried over magnesium sulfate. After filtration, the organic phase was concentrated under vacuum at room temperature to afford 4.6 g of crude flurithromycin. The crude material was dissolved in ethanol concentrated to 20 mL. This process was repeated two more times. After standing at 0° C. for one night, the product was filtered under vacuum, washed with 5 mL cold ethanol and dried under vacuum at 40° C. to afford 2.18 g (43% yield) of flurithromycin.

EXAMPLE 8

Preparation of (8S)-8-fluoroerythromycin A from anhydroerythromycin A with N-fluorobenzenesulfonimide in buffered acetic acid (sodium salt)

Anhydroerythromycin A (1 g, 1.4 mmole) was dissolved in glacial acetic acid (4 mL) at room temperature and the pH of the mixture was adjusted to 4.3 with 6N sodium hydroxide (approx. 2.5 mL) while the temperature was maintained below 20° C. N-fluorobenzenesulfonimide (0.44 g, 1.4 mmole) was added and stirring continued for an additional 18 hours at 22° C. Methylene chloride (10 mL) was added, the solution placed in an ice bath while the pH of the mixture was adjusted to 9 with 6 N sodium hydroxide (approx. 17 mL) and the temperature maintained below 20° C. Next, water (10 mL) was added, the layers separated and the aqueous layer washed an additional two times with methylene chloride (10 mL each). The combined organic phases were washed 2 to 4 times with 5% sodium hydroxide (10 mL each) and dried over magnesium sulfate. After filtration, the organic phase was concentrated under vacuum at room temperature to afford 0.88 g of crude flurithromycin. The crude material was dissolved in ethanol concentrated to 2 mL. This process was repeated two more times. After standing at 0° C. for one night, the product was filtered under vacuum, washed with 0.5 mL cold ethanol and dried under vacuum at 40° C. to afford 0.53 g (51% yield) of flurithromycin.

Comparative Example 1 (See Example 1)

Attempted Preparation of (8S)-8-fluoroerythromycin A from erythromycin A with N-fluorobenzenesulfonimide in buffered acetic acid and tetrahydrofuran as solvent.

Erythromycin A (5 g, 6.813 mmole) was dissolved in glacial acetic acid (20 mL) at room temperature and stirred for 2 hours. N-fluorobenzenesulfonimide (2.2 g, 6.813 mmole) dissolved in THF (4 mL) was added and stirring continued for an additional 18 hours at 22° C. The reaction was worked up in the same manner as Example 1 to afford only 0.93 g (7% yield) of crude flurithromycin.

Comparative Example 2 (See Example 4)

Attempted fluorination of 8,9-anhydroerythromycin A 6,9-hemiacetal with 1-chloromethyl-4-fluoro-1,4-diazoniabicyclo[2.2.2]octane bis(tetrafluoroborate) and acetic acid with acetonitrile as solvent.

An acetonitrile (4.2 mL) solution of 8,9-anhydroerythromycin A 6,9-hemiacetal (0.3 g, 0.42 mmole), 1-chloromethyl-4-fluoro-1,4-diazoniabicyclo[2.2.2]octane bis(tetrafluoroborate) (0.16 g, 0.46 mmole) and glacial acetic acid (0.04 mL, 0.84 mmole) was stirred at room temperature for 5 hours. The solution was evaporated, diluted with methylene chloride (5 mL), washed twice with 5% NaOH (5 mL), dried through $MgSO_4$ and evaporated to afford 0.26 g of a solid which contained 8.2% flurithromycin by HPLC.

Comparative Example 3 (See Example 4)

Attempted fluorination of erythromycin A N-oxide with 1-chloromethyl-4-fluoro-1,4-diazoniabicyclo[2.2.2]octane bis(tetrafluoroborate) with acetonitrile as solvent.

An acetonitrile (4.2 mL) solution of erythromycin A N-oxide (50 mg, 0.07 mmole), 1-chloromethyl-4-fluoro-1,4-diazoniabicyclo[2.2.2]octane bis(tetrafluoroborate) (26 mg, 0.07 mmole) and water (0.1 mL) was stirred at room temperature for 18 hours. The solution was diluted with methylene chloride (1 mL), washed twice with water (1 mL), dried through MgSO₄ and evaporated to afford only starting material.

Comparative Example 4 (See Example 6)

Attempted fluorination of erythromycin A N-oxide with N-fluoropyridinium pyridine heptafluorodiborate with nitromethane as co-solvent.

A nitromethane (1 mL) solution of erythromycin A N-oxide (50 mg, 0.407 mmole), N-fluoropyridinium pyridine heptafluorodiborate (25 mg, 0.07 mmole) was refluxed for 1 hour. The solution was diluted with methylene chloride (1 mL), washed twice with saturated NaHCO₃ (1 mL), dried through MgSO₄ and evaporated to afford only decomposition products.

We claim:

1. A process for preparing (8S)-8-fluoroerythromycins comprising contacting 8,9-anhydroerythromycin 6,9-hemiacetal or an N-oxide thereof with a carboxylic acid and an N-F fluorinating agent in the absence of an inert co-solvent for a time and temperature sufficient to obtain an (8S)-8-fluoroerythromycin.

2. The process of claim 1 wherein the N-F fluorinating agent is non pyridine based.

3. The process of claim 2 wherein the carboxylic acid has a pKa which is less than or about equal to that of acetic acid.

4. The process of claim 2 wherein the carboxylic acid is acetic acid.

5. The process of claim 2 wherein the carboxylic acid is buffered to a pH of 4–7.

6. The process of claim 2 wherein the carboxylic acid is buffered to a pH of 4–4.5.

7. The process of claim 1 wherein the N-F fluorinating agent is a fluorinated diazabicycloalkane.

8. The process of claim 1 wherein the N-F fluorinating agent is an N-fluorobenzenesulfonimide.

9. The process of claim 1 wherein the N-F fluorinating agent is a 1-substituted-4-fluoro-1,4-diazoniabicyclo[2.2.2]octane salt.

10. The process of claim 1 wherein the N-F fluorinating agent is N-fluoro- 1-chloromethyl-4-fluoro-1,4-diazoniabicyclo[2.2.2]octane bis(tetrafluoroborate).

11. The process of claim 1 wherein the N-F fluorinating agent is 1-hydroxyl-4-fluoro-1,4-diazoniabicyclo[2.2.2]octane bis(tetrafluoroborate).

12. The process of claim 1 wherein the N-F fluorinating agent is N-fluorodimethylsulfonimide.

13. The process of claim 1 wherein the 8,9-anhydroerythromycin 6,9-hemiacetal is prepared by reacting an erythromycin compound or an N-oxide thereof with a buffered carboxylic acid for a temperature and time sufficient to form the anhydroerythromycin prior to reaction with the N-F fluorination agent.

14. The process of claim 13 wherein the carboxylic acid has a pKa which is less than or about equal to that of acetic acid.

15. The process of claim 13 wherein the carboxylic acid is acetic acid.

16. The process of claim 13 wherein the carboxylic acid is buffered to a pH of 4–7.

17. The process of claim 13 wherein the carboxylic acid is buffered to a pH of 4–4.5.

18. The process of claim 13 wherein the N-F fluorinating agent is a fluorinated diazabicycloalkane.

19. The process of claim 13 wherein the N-F fluorinating agent is an N-fluorobenzenesulfonimide.

20. The process of claim 13 wherein the N-F fluorinating agent is N-fluoro- 1-chloromethyl-4-fluoro-1,4-diazoniabicyclo[2.2.2]octane bis(tetrafluoroborate).

21. The process of claim 13 wherein the N-F fluorinating agent is 1-hydroxyl-4-fluoro-1,4-diazoniabicyclo[2.2.2]octane bis(tetrafluoroborate).

22. The process of claim 13 wherein the N-F fluorinating agent is N-fluorodimethylsulfonimide.

* * * * *